US009060915B2

(12) United States Patent
Lutz et al.

(10) Patent No.: US 9,060,915 B2
(45) Date of Patent: Jun. 23, 2015

(54) METHODS FOR IMPROVING CELL THERAPY AND TISSUE REGENERATION IN PATIENTS WITH CARDIOVASCULAR DISEASES BY MEANS OF SHOCKWAVES

(75) Inventors: Andreas Lutz, Seefeld (DE); Harald Eizenhofer, Seefeld (DE); Andreas Michael Zeiher, Frankfurt (DE); Stefanie Dimmeler, Frankfurt (DE); Christopher Heeschen, Munich (DE); Alexandra Aicher, Frankfurt (DE)

(73) Assignee: Dornier MedTech Systems, GmbH (DE)

( * ) Notice: Subject to any disclaimer, the term of this patent is extended or adjusted under 35 U.S.C. 154(b) by 0 days.

(21) Appl. No.: 12/214,660

(22) Filed: Jun. 20, 2008

(65) Prior Publication Data
US 2008/0267927 A1 Oct. 30, 2008

Related U.S. Application Data

(63) Continuation of application No. 11/304,865, filed on Dec. 15, 2005, now abandoned.

(60) Provisional application No. 60/636,204, filed on Dec. 15, 2004.

(51) Int. Cl.
| A61K 48/00 | (2006.01) |
| A61H 23/00 | (2006.01) |
| A61B 17/22 | (2006.01) |
| A61K 38/18 | (2006.01) |
| A61K 38/19 | (2006.01) |
| A61K 35/44 | (2015.01) |
| A61B 17/00 | (2006.01) |
| A61B 18/00 | (2006.01) |

(52) U.S. Cl.
CPC ........ *A61H 23/008* (2013.01); *A61B 17/22004* (2013.01); *A61B 2017/00247* (2013.01); *A61B 2018/00392* (2013.01); *A61K 38/1866* (2013.01); *A61K 38/195* (2013.01); *A61K 35/44* (2013.01)

(58) Field of Classification Search
CPC .............. A61K 2300/00; A61K 35/44; A61K 38/1866; A61K 38/195
See application file for complete search history.

(56) References Cited

U.S. PATENT DOCUMENTS

| 48,847 A | 7/1865 | Smith |
| 1,750,129 A | 3/1930 | Romine |
| 2,324,702 A | 7/1943 | Hoffman |
| 2,578,505 A | 3/1948 | Carlin |
| 2,707,391 A | 5/1955 | McSkimin |
| 2,859,726 A | 11/1958 | Bouyoncos |
| 3,056,312 A | 10/1962 | Timpner |
| 3,249,177 A | 5/1966 | Chelminski |
| 3,406,302 A | 10/1968 | Lanyi |
| 3,505,880 A | 4/1970 | Riordan |
| 3,538,919 A | 11/1970 | Meyer |
| 3,555,880 A | 1/1971 | Menius, Jr. |
| 3,556,928 A | 1/1971 | Zolg |
| 3,588,801 A | 6/1971 | Leonard |
| 3,783,403 A | 1/1974 | Hook |
| 3,934,458 A | 1/1976 | Beretsky et al. |
| 3,946,829 A | 3/1976 | Mori |
| 3,997,853 A | 12/1976 | Morris |
| 4,189,026 A | 2/1980 | Elliot |
| 4,207,874 A | 6/1980 | Choy |
| 4,240,285 A | 12/1980 | Langdon |
| 4,272,733 A | 6/1981 | Walling |
| 4,286,168 A | 8/1981 | Carr |
| 4,286,455 A | 9/1981 | Ophir |
| 4,336,809 A | 6/1982 | Clark |
| 4,336,858 A | 6/1982 | Loyzim |
| 4,369,100 A | 1/1983 | Sawyer |
| 4,398,790 A | 8/1983 | Righini |

(Continued)

FOREIGN PATENT DOCUMENTS

| DE | 1769521 | 3/1973 |
| DE | 3723815 | 3/1973 |

(Continued)

OTHER PUBLICATIONS

Asahara et al (Science, 275: 964-967, 1997).*
Brehm et al (Herz, 27: 611-620, 2002).*
Herreros et al (European Heart Journal, 24: 2012-2020, 2003).*
Sylvester et al (Arch Surg. 139:93-99, 2004).*
Becker et al (The Neurologist, 9: 1-15, 2003).*
Pilgrim Harvard HealthCare 2002, PDF).*

(Continued)

*Primary Examiner* — Deborah Crouch
*Assistant Examiner* — Magdalene Sgagias
(74) *Attorney, Agent, or Firm* — King & Spalding LLP

(57) ABSTRACT

Improving cell therapy and tissue regeneration in a patient suffering from a cardiovascular or a neurological disease by treating a tissue of the patient with shock waves and/or applying to the patient a therapeutically effective amount of stem cells and/or progenitor cells. Such treatment increases expression of chemoattractants, pro-angiogenic factors, and pro-survival factors. The chemoattractants can be, for example, vascular endothelial growth factor (VEGF) or stromal cell derived factor 1 (SDF-1). For example, the treated tissue can be located in the patient's heart or in a skeletal muscle of the patient, and the shock waves can be extracorporeal shock waves (ESW) or intracorporeal shock waves. The cardiovascular disease can have an ischemic or non-ischemic etiology. For example, the cardiovascular disease can be a myocardial infarction, ischemic cardiomyopathy, or a dilatative cardiomyopathy. For example, the neurological disease can be a peripheral neuropathy or neuropathic pain.

14 Claims, 7 Drawing Sheets

(3 of 7 Drawing Sheet(s) Filed in Color)

(56) References Cited

U.S. PATENT DOCUMENTS

| | | |
|---|---|---|
| 4,493,653 A | 1/1985 | Robbins |
| 4,494,622 A | 1/1985 | Thompson |
| 4,526,168 A | 7/1985 | Hassler et al. |
| 4,546,960 A | 10/1985 | Abrams |
| 4,580,559 A | 4/1986 | L'Esperance |
| 4,586,512 A | 5/1986 | Do-huu |
| 4,620,546 A | 11/1986 | Aida |
| 4,639,923 A | 1/1987 | Tang |
| 4,641,912 A | 2/1987 | Goldenberg |
| 4,642,611 A | 2/1987 | Koerner |
| 4,658,828 A | 4/1987 | Dory |
| 4,669,472 A | 6/1987 | Eisenmenger |
| 4,671,254 A | 6/1987 | Fair |
| 4,672,969 A | 6/1987 | Dew |
| 4,693,244 A | 9/1987 | Daikuzono |
| 4,712,037 A | 12/1987 | Verbeek et al. |
| 4,721,108 A | 1/1988 | Heine |
| 4,756,016 A | 7/1988 | Grady |
| 4,798,196 A | 1/1989 | Nowacki |
| 4,807,626 A | 2/1989 | McGirr |
| 4,819,621 A | 4/1989 | Ueberle |
| 4,829,986 A | 5/1989 | Eichler |
| 4,962,752 A | 10/1990 | Reichenberger |
| 4,972,826 A | 11/1990 | Koehler |
| 5,046,483 A | 9/1991 | Ogura |
| 5,055,051 A | 10/1991 | Duncan |
| 5,060,650 A | 10/1991 | Wurster et al. |
| 5,067,493 A | 11/1991 | Inbar et al. |
| 5,070,861 A | 12/1991 | Einars |
| 5,072,722 A | 12/1991 | Granz |
| 5,072,723 A | 12/1991 | Viebach |
| 5,072,960 A | 12/1991 | Sperko |
| 5,090,401 A | 2/1992 | Schwieker |
| 5,143,073 A | 9/1992 | Dory |
| 5,144,953 A | 9/1992 | Wurster et al. |
| 5,149,030 A | 9/1992 | Cockrill |
| 5,191,560 A | 3/1993 | Lobentanzer et al. |
| 5,209,221 A | 5/1993 | Riedlinger |
| 5,209,222 A | 5/1993 | Viebach et al. |
| 5,243,985 A | 9/1993 | Aida et al. |
| 5,269,306 A | 12/1993 | Warnking et al. |
| 5,285,772 A | 2/1994 | Rattner |
| 5,287,856 A | 2/1994 | Treiber |
| 5,289,856 A | 3/1994 | Strock et al. |
| 5,301,659 A | 4/1994 | Brisson |
| 5,318,014 A | 6/1994 | Carter |
| 5,358,466 A | 10/1994 | Aida |
| 5,394,786 A | 3/1995 | Gettle |
| 5,395,592 A | 3/1995 | Bolleman |
| 5,409,002 A | 4/1995 | Pell |
| 5,435,311 A | 7/1995 | Umemura |
| 5,450,848 A | 9/1995 | Okazaki |
| 5,474,531 A | 12/1995 | Carter |
| 5,498,421 A | 3/1996 | Grinstaff |
| 5,524,620 A | 6/1996 | Rosenschein |
| 5,531,980 A | 7/1996 | Schneider |
| 5,543,553 A | 8/1996 | Stein |
| 5,567,414 A | 10/1996 | Schneider |
| 5,572,569 A | 11/1996 | Benoit |
| 5,635,207 A | 6/1997 | Grindstaff |
| 5,639,473 A | 6/1997 | Grindstaff |
| 5,642,898 A | 7/1997 | Wise |
| 5,643,553 A | 7/1997 | Schneider |
| 5,650,156 A | 7/1997 | Grindstaff |
| 5,658,239 A | 8/1997 | Dekmenico |
| 5,658,551 A | 8/1997 | Schneider |
| 5,658,892 A | 8/1997 | Flotte |
| 5,658,992 A | 8/1997 | Ehlers |
| 5,665,382 A | 9/1997 | Grindstaff |
| 5,665,383 A | 9/1997 | Grindstaff |
| 5,795,311 A | 8/1998 | Wess |
| 5,795,581 A | 8/1998 | Segalman |
| 5,810,748 A | 9/1998 | Ueberle |
| 5,836,898 A | 11/1998 | Schwieker |
| 5,864,517 A | 1/1999 | Hinkey |
| 6,036,611 A | 3/2000 | Bigo |
| 6,036,661 A | 3/2000 | Schwarze |
| 6,039,565 A | 3/2000 | Chou et al. |
| 6,066,123 A | 5/2000 | Li et al. |
| 6,119,034 A | 9/2000 | Herrmann |
| 6,135,357 A | 10/2000 | Herrin |
| 6,203,777 B1 | 3/2001 | Schroder |
| 6,206,835 B1 | 3/2001 | Spillman |
| 6,276,471 B1 | 8/2001 | Kratzenberg |
| 6,298,264 B1 | 10/2001 | Zhong |
| 6,361,747 B1 | 3/2002 | Dion |
| 6,386,560 B2 | 5/2002 | Calender |
| 6,408,614 B1 | 6/2002 | Eizenhofer |
| 6,416,740 B1 | 7/2002 | Unger |
| 6,424,863 B1 | 7/2002 | Flock |
| 6,428,532 B1 | 8/2002 | Doukas |
| 6,443,898 B1 | 9/2002 | Unger |
| 6,444,192 B1 | 9/2002 | Mattrey |
| 6,444,217 B1 | 9/2002 | Kwok |
| 6,461,586 B1 | 10/2002 | Unger |
| 6,465,006 B1 | 10/2002 | Zhang |
| 6,478,741 B2 | 11/2002 | Chiao et al. |
| 6,875,176 B2 | 4/2005 | Mourad et al. |
| 6,915,697 B2 | 7/2005 | Eizenhofer |
| 6,926,680 B2 | 8/2005 | Eizenhofer |
| 6,989,625 B2 | 1/2006 | Suzuki et al. |
| 7,107,997 B1 | 9/2006 | Moses et al. |
| 2001/0048732 A1 | 12/2001 | Wilson |
| 2002/0125664 A1 | 9/2002 | Eriksson |
| 2003/0017578 A1 | 1/2003 | Ueberle |
| 2003/0078523 A1 | 4/2003 | Burkhardt |
| 2003/0078671 A1 | 4/2003 | Lesniak et al. |
| 2003/0135205 A1 | 7/2003 | Davenport et al. |
| 2003/0191449 A1 | 10/2003 | Nash et al. |
| 2004/0059319 A1 | 3/2004 | Bohris |
| 2004/0191906 A1* | 9/2004 | Holzer .................. 435/383 |
| 2005/0010140 A1 | 1/2005 | Forssmann |
| 2007/0055157 A1 | 3/2007 | Bohris |

FOREIGN PATENT DOCUMENTS

| | | |
|---|---|---|
| DE | 7532292 | 3/1977 |
| DE | 3119295 | 12/1982 |
| DE | 3617032 | 1/1987 |
| DE | 3723815 | 6/1988 |
| DE | 3921808 | 6/1988 |
| DE | 3703335 | 8/1988 |
| DE | 3703338 | 8/1988 |
| DE | 3916093 | 11/1990 |
| DE | 3921808 | 1/1991 |
| DE | 4113697 | 1/1991 |
| DE | 9102394.7 | 6/1991 |
| DE | 4125950 | 11/1992 |
| DE | 4302537 | 4/1994 |
| DE | 4318237 | 4/1994 |
| DE | 9414692 | 9/1994 |
| DE | 4443495 | 6/1996 |
| DE | 4446192 | 7/1996 |
| DE | 19509004 | 10/1996 |
| DE | 4205030 | 4/1997 |
| DE | 29712035 | 10/1997 |
| DE | 69219342 | 11/1997 |
| DE | 19625164 | 1/1998 |
| DE | 19631246 | 2/1998 |
| DE | 19702829 | 7/1998 |
| DE | 19843680 | 9/1998 |
| DE | 20315924 | 9/1998 |
| DE | 19718511 | 7/1999 |
| DE | 1011800 | 3/2001 |
| DE | 10111800 | 3/2001 |
| DE | 10206193 | 7/2003 |
| DE | 102006037289 | 2/2008 |
| EP | 370336 | 8/1988 |
| EP | 369177 | 5/1990 |
| EP | 0369177 | 5/1990 |
| EP | 526758 | 2/1993 |
| EP | 0460536 | 10/1994 |
| EP | 511506 | 10/1996 |
| EP | 715831 | 2/1999 |

(56) References Cited

FOREIGN PATENT DOCUMENTS

| | | |
|---|---|---|
| JP | 02-215451 | 8/1990 |
| WO | WO 91/00358 | 1/1991 |
| WO | WO 96/20784 | 7/1996 |
| WO | WO 99/13943 | 3/1999 |
| WO | WO 99/42039 | 8/1999 |
| WO | WO 99/42176 | 8/1999 |
| WO | WO 00/02588 | 1/2000 |
| WO | WO 00/38580 | 7/2000 |
| WO | WO 00/69942 | 11/2000 |
| WO | WO 00/76406 | 12/2000 |
| WO | WO 01/48181 | 7/2001 |
| WO | WO 02/0515101 | 7/2002 |

OTHER PUBLICATIONS

Schafer et al, (Ultrasonic Symposium, 1623-1626, 1990).*
Office Action, dated Sep. 15, 2006, issued in U.S. Appl. No. 11/304,865.
Office Action, dated Apr. 11, 2007, issued in U.S. Appl. No. 11/304,865.
Office Action, dated Dec. 20, 2007, issued in U.S. Appl. No. 11/304,865.
Declaration of Prof. Andreas M. Zeiher dated Feb. 3, 2009.
Eguchi et al. "Endothelial progenitor cells for postnatal vasculogenesis," Clin Exp Nephrol. (2007) 11(1):18-25.
Lyngbaek et al. "Cardiac regeneration by resident stem and progenitor cells in the adult heart," Basic Res Cardiol (2007) 102:101-114.
Moehle et al. "The role of endothelium in the regulation of hematopoietic cell migration," Stem Cells 1998, 16 Suppl 1:159-65 (abstract only).
Wang et al. "Superoxide Mediates Shock Wave Induction of ERK-dependent Osteogenic Transcription Factor (CBFA1) and Mesenchymal Cell Differentiation toward Osteoprogenitors," J. Biol. Chem. (2002) 277:10931-7.
Wang et al. "Shock wave therapy induces neovascularization at the tendon-bone junction a study in rabbits," J Orthop Res. (2003) 21(6):984-9.
Itescu et al. "New directions in strategies using cell therapy for heart disease," J. Of Mol. Med., 81:288-296, 2003.
Menasche, "Cellular transplantation: hurdles remaining before widespread clinical use,"Current Opinion in Cardiology, 19(2): 154-161; 2004.
Wollert et al. "Clinical applications of stem cells for the heart," Circulation Research, 96: 151-163, 2005.
Assmus, B. et al. "Transpantation of Progenitor Cells and Regeneration Enhancement in Acute Myocardial Infarction (Topcare-Ami)," Circulation, vol. 106, pp. 3009-3017, 2002.
Uwatoku, T. et al. "Extracorporeal cardiac shock wave therapy improves left ventricular remodeling after acute myocardial infarction in pigs," Coronary Artery Disease 2007, 18:397-404.
Nishida, Takahiro, et al. "Extracorporeal Cardiac Shock Wave Therapy Markedly Ameliorates Ischemia-Induced Myocardial Dysfunction in Pigs in Vivo," Circulation, Vol/Iss: 110, pp. 3055-3061, Nov. 1, 2004.
A.A. Kocher, et al. "Neovascularization of Ischemic Myocardium by Human Bone-Marrow-Derived Angioblasts Prevents Cardiomyocyte Apoptosis, Reduces Remodeling and Improves Cardiac Function," Nature Medicine, Vol/Iss: vol. 7, No. 4. Pages: 430-436, Apr. 2001.
Kawamoto, Atsuhiko, et al. "Therapeutic Potential of Ex Vivo Expanded Endothelial Progenitor Cells for Myocardial Ischemia," Circulation, Vol/Iss: 103, pp. 634-637, 2001.
Jackson, K.A. "Regeneration of Ischemic Cardiac Muscle and Vascular Endothelium by Adult Stem Cells," Journal of Clinical Investigation, Vol/Iss: 107, pp. 1395-1402. 2001.
Abdel-LAT1F, a.H.Med et al. "Adult Bone Marrow-Derived Cells for Cardiac Repair," Arch Intern Med, Vol/Iss: 167 pp. 989-997, Nov. 29, 2007.
/M S / . Fa Wu, "Application of Hydroelastic Waves to the Removal of Small Gallstones," Transactions of the Amse, vol. 103, May 1981.
Bachmann, "Eswt und Sonographie der Stutz- und Bewegungsorgane," 1999, pp4-19.
Foster, "Flow Velocity Profile via Time-Domain Correlation: Error Analysis and Computer Simulation," IEEE Transactions on Ultrasonics, Ferroelectrics and Frequency Control, vol. 37, No. 2, May 1990.
Bonnefous, "Time Domain Formulation of Pulse-Doppler Ultrasound and Blood Velocity Estimation by Cross Correlation," Ultrasonic Imaging, 8:73-86, 1986.
Madsen, "Torso Section Phantom for Ultrasonic Imaging," Medical Physics. vol. 7, No. 1, Jan/Feb 1980.
R. F. Paterson et al., "Stone Fragmentation During Shock Wave Lithotripsy is Improved by Slowing the Shock Ff WaveRate: Studies With a New Animal Model," the Journal of Urology® vol. 168, pg. 2211-2215, Nov. 2002, Copyright 0 2002 by American Urological Association, Inc.®.
H. Wiksell, a.-C. Kinn, "Implications of Cavitation Phenomena for Shot Intervals in Extracorporeal Shock Wave Lithotripsy," British Journal of Urology, 1995, 75, pg. 720-723.
P. Hubert, et al., "Influence of Shock Wave Pressure Amplitude and Pulse Repetition Frequency on the Lifespan, Size and No. Of Transient Cavities in the Field of Electromagnetic Lithotripter," Phys. Med. Biol. 1998, 43, pg. 3113-3128.
R. F. Paterson, et al., "Slowing the Pulse Repetition Frequency in Shock Wave Lithotripsy (Swl) Improves Stone Fragmentation in Vivo," Proceedings of the 17th International Congress on Acoustics, Rome 2nd -7th Sep., 2001, pg. 200-201.
R. F. Paterson, et al., "An in Vivo Test of Shock Wave Rate Effect on Stone Fragmentation in Swl," the Journal of Urology® vol. 165, No. 5, Supplement, Jun. 6, 2001.
Matsumoto, Tomoyuki et al., Revascularization Engineering 1; Revascularization using Endothelail Progenitor Cells, Vascular Medicine, vol. 5, No. 6, 539-546, Dec. 10, 2004.
Fukumoto, Yoshihiro et al., "Medical Practice-Diagnosis of Circulatory Diseases for primary Care Doctors and Paradigm Shift in Therapies-Extracorporeal Shock Wave Therapy for Grave Ischemic Cardiac Disease," Therapy, vol. 86, No. 7, 2185-2188, Jul. 2004.
Tatsumi, Tetsuya et al., "Frontier Heart Disease Therapy by Regenerative Medicine-Basics & Clinical Study-Ii: Angiogenesis (1) Heart, Angiogenic Stem Cell Therapy for Ischemic Heart Disease," Cardiovascular Med-Sung, vol. 6, No. 3., 295-301, Aug. 2004.
Bohris et al., "Hit/Miss Monitoring of Eswl by Spectral Doppler Ultrasound", Ultrasound in Med. And Biology, vol. 29; pp. 705-712, 2003.
Chen, W., "A Light-Scattering Technique for Investigating the Destruction of Ultrasound Contrast Agents," IEEE Ultrasonics Symposium, pp. 1683-1686, 2001.
Coleman et al., " a survey of the Acoustic Output of Commercial Extracorporal Shock Wave Lithrotripters," Ultrasound in Med. And Biology, vol. 15, pp. 213-227, 1989.
Seitz, M., "Der Dioden Laser, Ex Vivo-Untersuchungen zu den Vaporisations -und Koasgulationseigenschalten," Uroge a, vol. 46(9), 1242-1247, 2007 a.
Wenst-Nordahl, G., "980-nm Diode laser: a Novel Laser Technology for Vaporization of the Prostrate, "Eur Urol, vol. 52, pp. 1723-1728, 2007.
Zhou et al., "Measurement of High Intensity Focused Ultrsound Fields by a Fibre Optyic Probe Hydrophone, "J. Acoust. Soc. Am., vol. 120, pp. 676-685, 2006.

* cited by examiner

Shock wave-treated right hindlimb      Untreated left hindlimb

Green: anti-VEGF staining
Blue: Topro-3 nuclear staining

Shock wave-treated (0.43 mJ/mm²) limb
followed by i.v. injection of CM-DiI+ EPCs Red:    CM-DiI+ EPCs
    Blue:   Topro-3 nuclear staining

* = p<0.05 versus no treatment; ** = p<0.05 versus EPC only

METHODS FOR IMPROVING CELL THERAPY AND TISSUE REGENERATION IN PATIENTS WITH CARDIOVASCULAR DISEASES BY MEANS OF SHOCKWAVES

RELATED APPLICATIONS

This application is a continuation of U.S. patent application Ser. No. 11/304,865 now abandoned filed Dec.15, 2005 and entitled "Methods For Improving Cell Therapy And Tissue Regeneration In Patients With Cardiovascular And Neurological Diseases By Means Of Shockwaves," which claims priority to U.S. Provisional Patent Application No. 60/636,204 filed Dec. 15, 2004 and entitled "Methods For Improving Cell Therapy And Tissue Regeneration In Patients With Cardiovascular And Neurological Diseases By Means Of Shockwaves." The complete disclosure of each of the above-identified priority applications is hereby fully incorporated herein by reference.

FIELD OF THE INVENTION

The present invention relates to methods for improving cell therapy in a patient. More specifically, the present invention relates to methods for improving cell therapy in patient who is suffering from a cardiovascular or a neurological disease by using shock waves as a therapeutic tool for targeting the recruitment of stem cells and/or progenitor cells to a tissue of the patient.

BACKGROUND OF THE INVENTION

Stem and progenitor cells derived from the bone marrow may play a role in ongoing endothelial repair (Kalka et al., 2000). Impaired mobilization or depletion of these cells may contribute to endothelial dysfunction and cardiovascular disease progression. Indeed, in healthy men, levels of circulating progenitor cells may be a surrogate biologic marker for vascular function and cumulative cardiovascular risk. Recent advances in basic science have also established a fundamental role for endothelial stem and progenitor cells in postnatal neovascularization and cardiac regeneration. Improvement of neovascularization after critical ischemia is an important therapeutic option after myocardial infarction or limb ischemia. Until recently, neovascularization of ischemic tissue in the adult was believed to be restricted to migration and proliferation of mature endothelial cells, a process termed "angiogenesis". Meanwhile, increasing evidence suggests that circulating stem and progenitor cells home to sites of ischemia and contribute to the formation of new blood vessels. In analogy to the embryonic development of blood vessels from primitive endothelial progenitors (angioblasts), this process is referred to as "vasculogenesis". The importance of circulating stem and progenitor cells is demonstrated by the fact that genetic inhibition of their recruitment inhibits tumor angiogenesis. Stem and progenitor cells can be mobilized from the bone marrow into the circulation by vascular endothelial growth factor ("VEGF") or stromal cell-derived factor ("SDF-1"). Both VEGF and SDF-1 are profoundly up-regulated in hypoxic tissue suggesting that VEGF and SDF-1 may constitute homing signals to recruit circulating stem and progenitor cells to enhance endogenous repair mechanisms after critical ischemia.

The present inventors have recently shown that infusion of bone marrow mononuclear cells derived from patients with ischemic heart disease is significantly less effective in improving perfusion of ischemic tissue in a hind limb ischemia animal model. Moreover, bone marrow cells of patients with ischemic heart disease reveal a reduced colony forming activity and an impairment of migratory response towards VEGF and SDF-1, which are potent chemoattractive and mobilizing agents (Heeschen C et al., Circulation 2004; 109(13): 1615-22.) Moreover, the present inventors were also able to demonstrate that in experimental models of tissue ischemia, recruitment of systemically infused stem/progenitor cells is significantly lower as compared to the recruitment of stem/progenitor cells derived from healthy donors. While in patients with acute coronary syndromes, the present inventors have observed a marked increase in systemic VEGF levels within 10 hours after onset of symptoms (Heeschen et al. Circulation 2003; 107(4):524-30), in another set of patients with acute myocardial infarctions, systemic VEGF levels three days after the acute event had already decreased and did not significantly differ from levels measured in patients without coronary heart disease (Lee et al. NEJM 2000; 342:626-33). Taken together, these data suggest that, in patients with chronic tissue damage such as old myocardial infarction, the recruitment of stem/progenitor cells will be markedly reduced due to the low expression of chemoattractant factors in the target tissue as well as due to the low functional activity of autologous stem/progenitor cells from patients with cardiovascular risk factors.

Extracorporeal shock waves ("ESW") are generated by high voltage spark discharge under water. This causes an explosive evaporation of water, producing high energy acoustic waves. By focusing the acoustic waves with a semi-ellipsoid reflector, the waves can be transmitted to a specific tissue site (Ogden et al., 2001). ESW have been found beneficial in certain orthopedic conditions. The interactions of ESW with the targeted tissue are manifold: mechanical forces at tissue interfaces related to different acoustic impedances, as well as micro-jets of collapsing cavitation bubbles are the primary effects. However, the cellular and biochemical mechanisms, by which these physical effects may enhance healing of fractures, remain to be determined. It has been scintigraphically and sonographically implicated that local blood flow and metabolism of bone and Achilles tendon are positively affected by ESW treatment (Maier et al., 2002).

ESW therapy has shown to be effective in the treatment of orthopedic conditions including non-union of long bone fracture, calcifying tendonitis of the shoulder, lateral epicondylitis of the elbow, proximal plantar fasciitis, and Achilles tendonitis (Kruger et al., 2002). The success of shock wave therapy ranges from 80% for non-unions of long bone fractures to 15-90% for tendinopathies of the shoulder, elbow and heel. In addition, the short-term results of shock wave therapy for avascular necrosis of the femoral head appear encouraging. Shock wave therapy also showed a positive effect in promoting bone healing in animal experiments. Despite the success in clinical application, the exact mechanism of shock wave therapy remains unknown. Recent experiments in dogs demonstrated, however, that shock wave therapy enhanced neovascularization at the tendon-bone junction (Wang et al., 2002). It was hypothesized that shock wave therapy may have the potential to induce the ingrowth of new blood vessels and improvement of blood supply that lead to tissue regeneration. Indeed, a recent study in rabbits showed that shock wave therapy induces the ingrowth of neovessels and tissue proliferation associated with the early release of angiogenesis-related factors including endothelial nitric oxide synthase (eNOS) and VEGF at the tendon-bone junction in rabbits (Wang et al., 2003). Therefore, the mechanism of shock wave therapy may involve the early release of angiogenic growth factors and subsequent induction of cell proliferation and formation of neovessels at the tendon-bone junction. The occurrence of neovascularization may lead to the improvement of blood supply and play a role in tissue regeneration at the tendon-bone junction.

It was also reported that the ESW-induced VEGF-A elevation in human osteoblasts is mediated by Ras-induced superoxide and ERK-dependent HIF-1 activation.

Further, it has been demonstrated that ESW enhance osteogenic differentiation of mesenchymal stem cells in vitro as well as bone union of segmental defect in vivo through superoxide-mediated signal transduction (Wang et al., 2002a). These data indicate that the microenvironment of the defect is indeed responsive to physical ESW stimulation. Subsequent experimental studies demonstrated that mesenchymal stem cells adjacent to the segmental defect were subject to three consecutive events after ESW treatment: intensive recruitment, proliferation, and chondrogenic as well as osteogenic differentiation (Chen et al., 2004). The utilized energy for ESW treatment (0.16 mJ/mm$^2$ EFD) did not induce side effects in rats. A major limitation of this in vivo study is that the morphological techniques utilized for the identification of mesenchymal stem cells lack specificity. Only few other studies of bone repair have monitored mesenchymal stem cells of rats, as specific markers for such cells are scarce.

Regarding the use of ESW for treating tissues other than bone, it was shown that ESW therapy ameliorates ischemia-induced myocardial dysfunction in pigs in vivo (Nishida et al., 2004).

It is noted that no prior art exists which discloses or suggests a possible link between ESW therapy and the use of stem and progenitor cells for cell therapy.

In summary, post infarction heart failure remains a major cause of morbidity and mortality in patients with coronary heart disease. Although prompt reperfusion of the occluded artery has significantly reduced early mortality rates, ventricular remodeling processes characterized by progressive expansion of the infarct area and dilation of the left ventricular cavity result in the development of heart failure in a sizeable fraction of patients surviving an acute myocardial infarction. The major goal to reverse remodeling would be the stimulation of neovascularization as well as the enhancement of regeneration of cardiac myocytes within the infarct area.

Peripheral neuropathy describes damage to the peripheral nerves. It may be caused by diseases of the nerves or as the result of systemic illnesses. Many neuropathies have well-defined causes such as diabetes, uremia, AIDS, or nutritional deficiencies. In fact, diabetes is one of the most common causes of peripheral neuropathy. Other causes include mechanical pressure such as compression or entrapment, direct trauma, fracture or dislocated bones; pressure involving the superficial nerves (ulna, radial, or peroneal); and vascular or collagen disorders such as atherosclerosis, systemic lupus erythematosus, scleroderma, and rheumatoid arthritis. Although the causes of peripheral neuropathy are diverse, they produce common symptoms including weakness, numbness, paresthesia (abnormal sensations such as burning, tickling, pricking or tingling) and pain in the arms, hands, legs and/or feet. A large number of cases are of unknown cause.

Therapy for peripheral neuropathy differs depending on the cause. For example, therapy for peripheral neuropathy caused by diabetes involves control of the diabetes. In entrapment or compression neuropathy, treatment may consist of splinting or surgical decompression of the ulnar or median nerves. Peroneal and radial compression neuropathies may require avoidance of pressure. Physical therapy and/or splints may be useful in preventing contractures (a condition in which shortened muscles around joints cause abnormal and sometimes painful positioning of the joints).

Ischemic peripheral neuropathy is a frequent, irreversible complication of lower extremity vascular insufficiency. It has been shown that ischemic peripheral neuropathy can be prevented and/or reversed by gene transfer of an endothelial cell mitogen (e.g. VEGF) designed to promote therapeutic angiogenesis (Schratzberger P, et al.). The major goal to reverse vascular insufficiency would thus be the stimulation of angiogenesis and the regeneration of the vascular tissue within the area affect by peripheral neuropathy.

The technical problem underlying the present invention in thus to enhance the cell therapy and regeneration of tissues affected by a cardiovascular or a neurological disease.

According to the invention, this problem is solved by the provision of a method for improving cell therapy in a patient suffering from a cardiovascular disease or a neurological disease comprising a treatment by means of shock waves of an tissue of the patient affected by the disease, which tissue is targeted for cell therapy.

SUMMARY OF THE INVENTION

The present invention provides, in part, a therapeutic tool improving the targeted recruitment of stem and progenitor cells in patients undergoing cell therapy.

The present invention relates to methods for improving cell therapy in a patient who is suffering from a cardiovascular or a neurological disease and is undergoing cell therapy by using shock waves as a therapeutic tool for targeting the recruitment of stem cells and/or progenitor cells to a tissue of the patient. The present invention also relates to methods for improving tissue regeneration in a patient suffering from a cardiovascular or neurological disease by treating a tissue of the patient affected by the disease using shock waves. Also provided are methods for treating a cardiovascular or neurological disease in a patient comprising the treatment of a tissue of the patient affected by the disease by means of shock waves, and applying to the patient a therapeutically effective amount of stem cells and/or progenitor cells. The present invention further also relates to the use of stem cells and/or progenitor cells for preparing a pharmaceutical composition for treating a patient suffering from a cardiovascular disease or a neurological disease, wherein the patient is subjected to a treatment with shock waves before, during, or after administration of the stem cells and/or progenitor cells.

The present inventors have recently shown that autologous stem and progenitor cells in patients with cardiovascular risk factors have a reduced ability to home and migrate to damaged tissue. Since the expression of chemoattractant factors in chronically injured tissue is markedly reduced as compared to acute injury, the overall recruitment of stem/progenitor cells in patients with cardiovascular risk factors is impaired. The invention involves the treatment of tissue that is targeted for therapy with stem and progenitor cells by means of shock waves to increase the expression of chemoattractants (i.e. factors mediating the attraction of circulating stem and progenitor cells, e.g. SDF-1α, VEGF, PlGF) and pro-angiogenic factors (i.e. factors stimulating pre-existing endothelial cells to form new vessels, e.g. HIF-1α, VEGF, PlGF) as well as pro-survival factors (i.e. factors inhibiting apoptosis/programmed cell death, e.g. HGF, IGF, VEGF). The increased expression of chemoattractant and pro-angiogenic factors will improve the recruitment of systemically infused stem and/or progenitor cells, and enhanced expression of pro-survival factors will improve the microenvironment for cells directly administered into the target tissue. The homing of stem and progenitor cells will be enhanced. Thereby, shock wave treatment of the targeted tissue will enhance the therapeutic effect of cell therapy.

By combining the application of extracorporeal shock waves ("ESW") and the application of stem cells and/or progenitor cells, the regeneration of cardiovascular and neurological diseases may be improved. The combination of ESW and the application of stem cells and/or progenitor cells may be used to treat cardiovascular and neurological diseases.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF EXEMPLARY EMBODIMENTS

Figure 1:
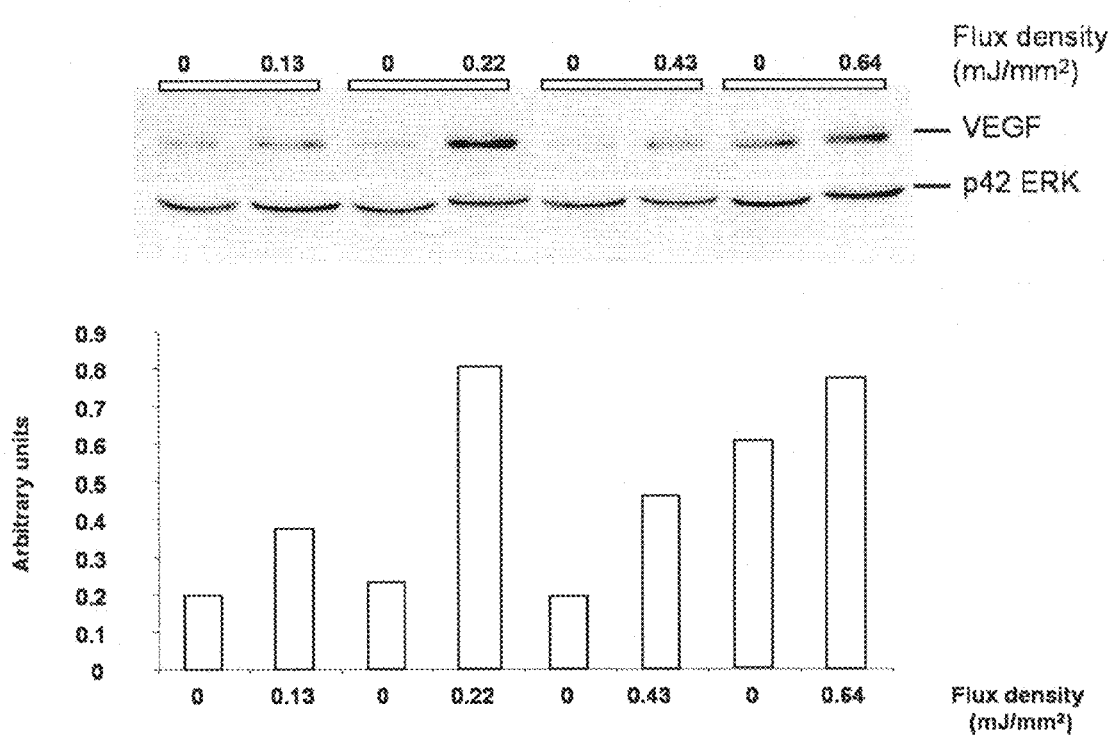
FIG. 1 is a block diagram depicting shock wave-induced vascular endothelial growth factor ("VEGF") expression in rat hindlimb muscles detected by Western blot, according to an exemplary embodiment of the invention.

In one aspect, the invention is related to a method for improving cell therapy in a patient suffering from a cardiovascular disease or a neurological disease comprising a treatment by means of shock waves of a tissue of the patient affected by the disease, which tissue is targeted for cell therapy.

In another aspect, the invention relates to a method for improving the tissue regeneration in a patient suffering from a cardiovascular disease or a neurological disease comprising the steps of treating a tissue of the patient affected by the disease by means of shock waves, and applying to the patient a therapeutically effective amount of stem cells and/or progenitor cells.

In yet another aspect, the invention is related to a method for treating a cardiovascular disease or a neurological disease in a patient comprising the steps of treating a tissue of the patient affected by the disease by means of shock waves, and applying to the patient a therapeutically effective amount of stem cells and/or progenitor cells.

In a preferred embodiment of the methods according to the invention, the treatment of the patient by shock waves is carried out prior to the administration of the stem and/or progenitor cells. However, a simultaneous application of both shock waves and stem/progenitor cells and a subsequent application of shock waves (following the administration of the stem/progenitor cells) is also contemplated.

In a further aspect, the invention relates to a use of stem and/or progenitor cells for preparing a pharmaceutical composition for treating a patient suffering from a cardiovascular disease or neurological disease, wherein the patient is subjected to a treatment with shock waves before, during, or after administration of the stem and/or progenitor cells.

The term "cell therapy" refers to the transplantation of cells to replace or repair damaged tissue and/or cells. Cell therapy involves the use of blood transfusions and bone marrow transplants, as well as injections of cellular materials.

Within the meaning of the present invention, the term "shock waves" is used interchangeably with the term "acoustical pressure pulse".

The term "stem cell" refers to an unspecialised cell that is capable of replicating or self-renewing itself and developing into specialized cells of a variety of cell types. The product of a stem cell undergoing division is at least one additional cell that has the same capabilities as the original cell. The term "stem cell" is intended to encompass embryonal and adult stem cells, totipotent and pluripotent cells, and autologous cells, as well as heterologous cells.

The definition of "progenitor cell" (also known as a precursor cell) is intended to encompass cells which are yet undifferentiated but may already be committed to a specific cell type (e.g. endothelial progenitor cells are committed to differentiate into endothelial cells).

In one embodiment of the invention, the patient's disease is a cardiovascular disease. In a specific embodiment, the cardiovascular disease has a non-ischemic etiology. An example of a cardiovascular disease with a non-ischemic etiology which can be treated by the methods according to the invention is dilatative cardiomyopathy. Alternatively, the cardiovascular disease may have an ischemic etiology. Cardiovascular diseases with an ischemic etiology which may be improved by cell therapy include myocardial infarctions and ischemic cardiomyopathies. Chronic ischemic cardiomyopathy is particularly preferred.

In another embodiment of the invention, the patient's disease is a neurological disease. In a preferred embodiment, the neurological disease is peripheral neuropathy or neuropathic pain.

Thus, preferably, the affected tissue is located in the heart or in a skeletal muscle.

In a further embodiment of the invention, the expression of at least one chemoattractant factor is induced in the affected tissue of the patient. The term "chemoattractant factor" is used herein to refer to a factor activating the movement of individual cells, in response to a chemical concentration gradient.

Preferably, the at least one chemoattractant factor is vascular endothelial growth factor, VEGF, or stromal cell derived factor 1, SDF-1.

The shock waves used in the methods and uses according to the invention preferably are extracorporeal shock waves which may, for instance, be applied extra-thoracal. However, also intracorporeal shock waves (delivered e.g. trans-esophageal) and endoscopic shock waves (delivered e.g. intraluminal such as in the artery) are contemplated. Moreover, the shock waves may be applied during open surgery (intraoperative).

In a preferred embodiment, 50, 100, 150, or 200 shocks per area and/or a total number of 100, 250, 500, 1000, or 1500 shocks per treatment are applied. Preferably, shocks with an energy of 0.05, 0.09, 0.13; 0.22, 0.36, or 0.50 mJ/mm$^2$ are applied. The shock waves may be applied once or several times prior to cell therapy; an application once or twice prior to cell therapy is preferred. Preferably, the shock waves are applied several hours before the start of the cell therapy; an application 24 h, 36 h, or 48 h prior to cell injection is particularly preferred. Alternatively, the shock waves may be exclusively or additionally be applied during cell therapy and/or after the start of the cell therapy.

In one embodiment, the stem and/or progenitor cells which are used in the methods and uses according to the invention are embryonic or umbilical cord-blood derived cells.

Alternatively, the stem and/or progenitor cells are adult cells. Adult stem and/or progenitor cells can be derived from bone marrow, peripheral blood, and organs. For example, the cells can be derived from healthy donors or patients suffering from coronary heart disease.

For use in the methods and uses according to the present invention, the stem and/or progenitor cells are isolated and, optionally, cultivated ex vivo before being applied.

In specific embodiments, the following stem and/or progenitor cells may be used in the methods and uses according to the invention:

CD34+CD133+bone marrow-derived stem cells
CD34+CD38−bone marrow-derived stem cells
CD34+CD45+bone marrow-derived progenitor cells
CD34+KDR+bone marrow-derived endothelial progenitor cells
CD34−CD45−bone marrow-derived mesenchymal stem cells (MSC)
eNOS+KDR+CD105+VE-Cadherin+vWF+CD45+peripheral blood-derived endothelial progenitor cells
stage-specific embryonic antigen, SSEA-4+Oct4+embryonic stem cells
CD34+CD133+cord blood-derived stem cells
CD34+CD45+cord blood-derived stem cells.

The stem and/or progenitor cells used in the methods and uses according to the invention may be applied by way of systemic infusion, local arterial infusion, venous infusion, and/or by direct injection into the affected tissue. For the purpose of delivery, the cells may further be encapsulated in microspheres (targeted drug delivery). Contrast agents used for ultrasound are examples for useful encapsulation agents. The cells may then be released from the microspheres at the targeted tissue using ultrasound (acoustic energy).

Recent data suggests that, in patients with chronic tissue damage, such as old myocardial infarction, the recruitment of stem/progenitor cells is markedly reduced due to the low expression of chemoattractant factors in the affected tissue. However, treatment of the targeted tissue by single or repetitive exposure to shock waves will (re)induce the expression of pro-angiogenic, chemoattractant, and pro-survival factors such as VEGF and SDF-1 and, thereby, will enhance the recruitment of stem/progenitor cells. Since the treatment effect of cell therapy is directly proportional to the number of recruited cells, this enhanced recruitment and survival of stem/progenitor cells after treatment with shock waves will increase the therapeutic benefit that the individual patients will derive from cell therapy for tissue regeneration and tissue.

A prerequisite for the success of cell therapy is the homing and, thus, engraftment of transplanted cells into the target area, especially if an intravascular route of administration is chosen. The present inventors have now shown that the migratory capacity of adult progenitor cells towards their physiological chemo-attractant reflects their homing capacity into the ischemic/infarcted area. Indeed, the experimental studies conducted by the present inventors which are shown in the present invention demonstrate that, in the hind limb ischemia model of nude mice, homing of transplanted cells to the ischemic tissue and improvement of neovascularization induced by intravenous infusion of human progenitor cells closely correlates with SDF-1-induced migratory capacity for bone marrow-derived cells, as well as with VEGF-induced migratory capacity for blood-derived progenitor cells, respectively. Functional impairment of stem and progenitor cells from aged individuals and patients with cardiovascular diseases, as well as the reduced expression of pro-angiogenic, chemoattractant, and pro-survival factors in the targeted tissue may limit the beneficial effects of clinical cell therapy. As shown in the present examples, treatment of the targeted tissue by means of shock waves will facilitate stem and progenitor recruitment and survival and, thus, will enhance the therapeutic effect of cell therapy.

Specifically, the present inventors identified that:

a. enhancing the recruitment of stem/progenitor cells is a novel target for improving the clinical outcome after autologous cell therapy in aged individuals and patients with cardiovascular risk factors;

b. a high level of expression of pro-angiogenic, chemoattractant and pro-survival factors can be restored by treatment of the target tissue with shock waves;

c. treatment of chronically injured tissue by single or repetitive administration of shock wave prior to autologous cell therapy improves the clinical outcome after cell therapy.

The following Figures and Examples are intended for illustration of the present invention only, and should not be construed as limiting the scope of the invention.

EXAMPLES

1. Materials for Preparing Endothelial Progenitor Cells from Peripheral Blood

As the starting material for preparing endothelial progenitor cells, peripheral blood was freshly drawn and collected in heparin monovettes (10 ml).

The following materials were used in the examples described below.

Dulbecco's Phosphate Buffered Saline without calcium and magnesium (Cat. No. H-15-002) was used for suspension of the cells for injection. PAA was purchased from Laboratories GmbH (Pasching, Austria). EGM Bullet Kit (EBM medium) (Cat. No. CC-3124) and 1,1'-dioctadecyl-3,3,3',3'-tetramethylindocarbocyanine-labeled acetylated low-density lipoprotein (Dil-Ac-LDL) (Cat. No. #4003) was obtained from CellSystems (St. Katharinen, Germany). Fetal Bovine Serum (Cat. No. 10270-106) was obtained form Invitrogen GmbH (Karlsruhe, Germany). Biocoll Separating Solution, Density: 1.077 (Cat. No. L6115) was purchased from Biochrom AG (Berlin, Germany). Human fibronectin, 1 mg/ml (Cat. No. F-0895) and lectin from *Ulex europaeus* (Cat. No. L-9006) was purchased Sigma (Taufkirchen, Germany). Human recombinant vascular endothelial growth factor (VEGF) (Cat. No. 100-20) was acquired from Cell Concepts (Umkirch, Germany). EDTA disodium salt dihydrate (Cat. No. A1104) was obtained from AppliChem (Darmstadt, Germany). TÜRK'S solution (Cat. No. 1.09277.0100) was purchased from Merck (Darmstadt, Germany).

2. Cell Preparation 2.1 Isolation of Endothelial Progenitor Cells from Peripheral Blood Mononuclear cells (MNC) are separated from freshly collected peripheral blood or buffy coats from the blood donation center using Ficoll gradient centrifugation. First, 15 ml Biocoll separation solution are provided per 50 ml tube. The peripheral blood (PB) is diluted with PBS (PB 1:1 or buffy coats 1:4). Carefully and slowly, 25 ml of the diluted blood are overlayed on 15 ml of the Biocoll separation solution. The tube is centrifugated at 800×g for 20 min at room temperature without brake. This is an important step to separate the mononuclear cells (in the interphase) from erythrocytes and granulocytes (pellet) and platelets in the upper serum phase. Meanwhile, wells are coated with 10 µg/ml human fibronectin in PBS, and the wells are incubated for at least 30 min at room temperature. The mononuclear cells are pipetted from the interphase carefully in a new 50 ml tube. PBS is added to 50 ml to wash the cells. The cells were centrifugated at 800×g for 10 min at room temperature (with brake). The supernatant was removed and the cell pellet was resuspended in 50 ml PBS. The cells were centrifugated at 800×g for 10 min at room temperature (with brake), the supernatant was removed and the cell pellet was resuspended in 10 ml PBS. An aliquot of the cells (50 µl) was diluted (1:10) with TÜRK'S solution and counted. PBS was added to the remaining cells in the 50 ml tube to wash the cells again, following centrifugation at 800×g, 10 min, room temperature, with brake. The washing steps should be performed for at least 3 times, but should be repeated until the supernatant becomes clear (altogether 3-5 times).

Then, the supernatant is removed and the cell pellet is resuspended in culture medium (endothelial basal medium supplemented with 20% FBS, epidermal growth factor (10 µg/mL), bovine brain extract (3 µg/mL), gentamicin (50 µg/mL), hydrocortisone (1 µg/mL), VEGF (100 ng/ml) to a cell concentration of $8 \times 10^6$ cells/ml medium. Fibronectin is then removed from the dishes. Next, the cells are added to the fibronectin-coated wells at a density of approx. $2.1 \times 10^6$ cells/$cm^2$ (per 24 well plate: $4 \times 10^6$ cells in 500 µl medium per well; per 12 well plate: $8 \times 10^6$ cells in 1 ml medium per well; per 6 well plate: $20 \times 10^6$ cells in 2.5 ml medium per well). The cells are incubated for 3 days at 37° C. and 5% $CO_2$. Three days after cultivation, the non-adherent cells were removed by thoroughly washing the cells with PBS. Fresh culture medium was added for 24 h before starting the experiments. Approximately 0.5-1% of the initially applied mononuclear cells becomes adherent endothelial progenitor cells (EPCs).

2.2. Labeling with Red Fluorescent Cell Tracker CM-Dil

EPCs were washed with PBS, trypsinized for 2 min, then the reaction was stopped with serum-containing RPMI medium. Detached EPCs were washed again with PBS, incubated with CM-Dil (Molecular Probes) diluted in PBS (1:100) for 5 min at 37° C., followed by incubation for 15 min on ice. After washing, $1 \times 10^6$ CM-Dil-labeled EPCs were injected into the jugular vein of nude rats pre-treated with shock wave therapy.

3. Application of Shock Wave Treatment

Shock waves were applied at graded doses of flux density (0.13-0.64 $mJ/mm^2$; 3 Hz; 500 impulses) to the upper right hind limb of nude rats. The energy was focused on the upper limb, while moving the focus distally for 2 mm after every 100 impulses.

3.1 Shock Wave Treatment to Upregulate Chemoattractant Factors in the Rat Limb

To assess whether shock wave treatment up-regulates proangiogenic growth factors such as VEGF, which is chemoattractant for VEGF receptor 1 or 2 positive stem and progenitor cells that are injected after 24 h, shock wave treatment was performed. The right hind limb of nude rats was treated with a flux density of 0.13, 0.22, 0.43, and 0.64 $mJ/mm^2$ (FIG. 1). The left hind limb was used as a negative control (0 $mJ/mm^2$). After 24 h, the shock wave-induced up-regulation of VEGF protein expression was analyzed in the treated versus the untreated hind limb by means of Western blotting. It was found that flux densities up to 0.43 $mJ/mm^2$ yielded favorable VEGF protein expression ratios between shock wave-treated versus untreated limbs, resulting in at least 2-fold induction of VEGF protein expression. The best ratio (more than 2-fold induction) was obtained by using 0.22 $mJ/mm^2$. Flux densities higher than 0.64 $mJ/mm^2$ also strongly enhanced background levels of VEGF protein expression so that insufficient ratios were obtained to induce treatment-specific VEGF protein induction. These data suggest that shock wave treatment should not be applied over a threshold value to avoid unspecific VEGF protein induction of the contralateral hind limb.

Animal model. Immunodeficient female nude rats (5 to 7-wk old) underwent shock wave treatment with a flux density of 0.13, 0.22, 0.43, and 0.64 $mJ/mm^2$, which was delivered to the right hind limb. The contralateral left hind limb did not receive shock wave treatment. Twenty-four hours later, rats were sacrificed and the adductor muscle of the right and left hind limbs were removed, frozen in liquid nitrogen, and minced in a mortar using 1 ml protein lysis buffer (20 mmol/L Tris (pH 7.4), 150 mmol/L NaCl, 1 mmol/L EDTA, 1 mmol/L EGTA, 1% Triton, 2.5 mmol/L sodium pyrophosphate, 1 mmol/L β-glycerophosphate, 1 mmol/L Na3VO4, 1 µg/mL leupeptin and 1 mmol/L phenylmethylsulfonyl fluoride) for 15 min on ice.

Western blot analysis. Proteins (40 µg/lane) were loaded onto SDS-polyacrylamide gels and blotted onto PVDF membranes. After blocking with 3% bovine serum albumin (BSA) at room temperature for 2 h, the anti-rat VEGF antibody (R&D, Germany) was incubated in TBS (50 mM Tris/HCl, pH 8; 150 mM NaCl, 2.5 mM KCl)/0.1% Tween-20/3% BSA for 2 h. Enhanced chemiluminescence was performed according to the instructions of the manufacturer (Amersham, Germany). Then, the blots were reprobed with the ERK antibody (Biolabs, Schwalbach, Germany) as a loading control. The autoradiographies were scanned and semiquantitatively analyzed.

Figure 2A:
FIG. 2A is a representative image of shock wave-induced VEGF expression in rat hind limb muscles detected by VEGF staining on frozen sections, according to an exemplary embodiment of the invention.
Figure 2A:
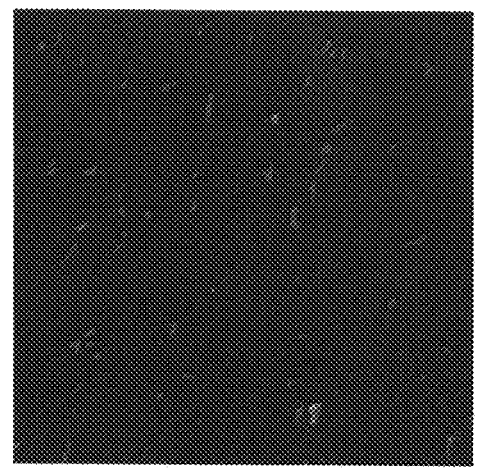
Figure 2B:
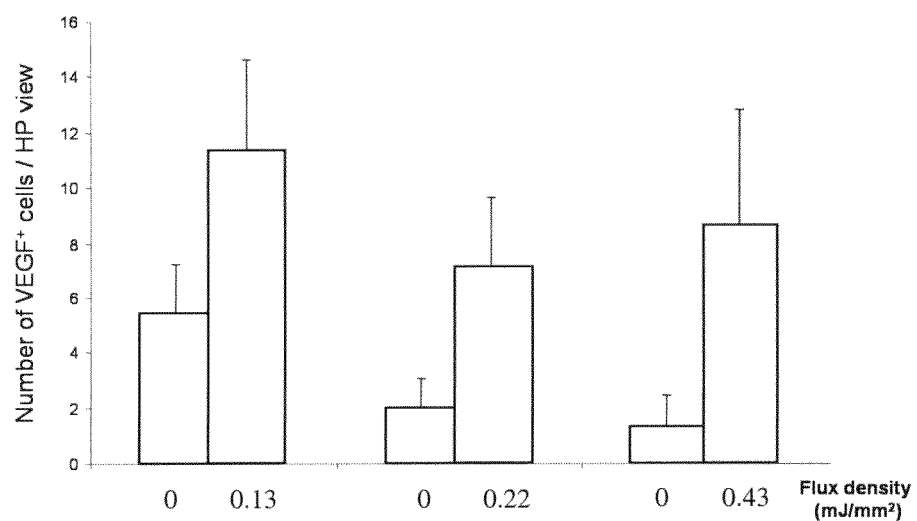
FIG. 2B is a block diagram depicting shock wave-induced VEGF expression in rat hind limb muscles detected by VEGF staining on frozen sections, according to an exemplary embodiment of the invention.

To evaluate VEGF protein expression in tissue sections of the right hind limb of shock wave-treated nude rats, cryosections of shock wave-treated versus untreated hind limb muscles were stained for VEGF expression (FIG. 2a). VEGF expression was detected as cytoplasmic and secreted VEGF staining (green fluorescence) with respect to nuclear staining (blue fluorescence). Since flux densities higher than 0.43 $mJ/mm^2$ led to high unspecific background levels of VEGF expression, only flux densities between 0.13 $mJ/mm^2$ and 0.43 $mJ/mm^2$ were used (FIG. 2b). Similar to the VEGF expression ratios obtained by Western blotting, flux densities of 0.22 $mJ/mm^2$ induced a more than 2-fold induction of VEGF protein expression compared with flux densities of 0.13 $mJ/mm^2$ resulting in lower ratios. In contrast to the results obtained by Western blotting, the best ratio was obtained by 0.43 $mJ/mm^2$.

Histological analysis. Tissue samples of nude rats treated with or without shock waves as described above and were harvested after 24 h and frozen in liquid nitrogen pre-chilled with 2-methylbutane in OCT (TissueTec, Sakura, The Netherlands). 10-μm sections were cut and immunostaining was performed. Anti-rat VEGF (R&D, Wiesbaden, Germany) was directly labeled with Alexa488 (green fluorescence) using Alexa Fluor R 488 antibody labeling kit (Molecular Probes, Eugene, Oreg., USA). Nuclear staining was performed using Topro-3 (Molecular Probes).

For the quantification of shock wave-induced VEGF expression in rat hind limb muscles (M. adductor and M. semimembraneous), the number of VEGF$^+$ cells per high power (HP) view was determined for 0.13, 0.22, and 0.43 mJ/mm$^2$.

3.2 Shock Wave-faciliated Recruitment of Systemically Infused Endothelial Progenitor Cells To test the hypothesis that shock wave-induced up-regulation of chemoattractant factors such as VEGF might indeed enhance the recruitment of systemically injected human EPCs, EPCs were labeled with a red fluorescent cell tracker and infused intravenously 24 h after shock wave therapy of the right hind limb. Since the best results for VEGF staining in cyrosections had been obtained using energy of 0.43 mJ/mm$^2$, the following experiments were performed using the same flux density.

Animal model. Twenty-four hours after shock wave treatment of the right hind limb, CM-Dil$^+$ (red fluorescent) human EPCs (1×10$^6$) were intravenously injected. The animals were sacrificed after 72 h and the tissue was evaluated for red fluorescent EPCs incorporated into vessel structures. The number of red fluorescent cells in the shock wave-treated right versus the untreated left hind limb was analysed.

Figure 3A:
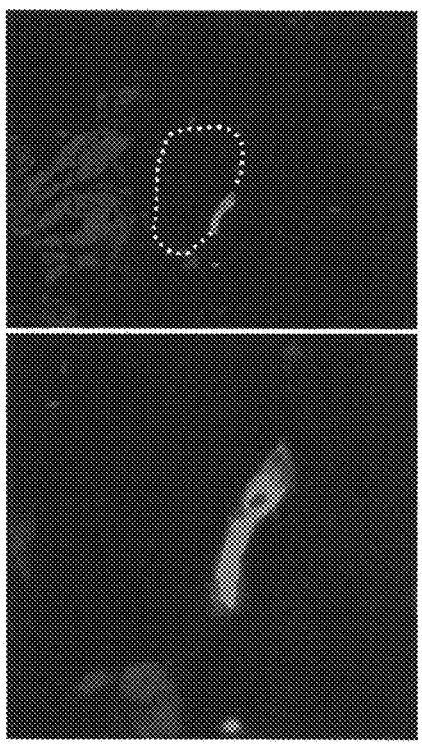
FIG. 3A is a representative image of detection of intravenously injected endothelial progenitor cells ("EPCs") after shock wave treatment, wherein 10-μm frozen sections were analyzed for EPCs (red fluorescence) and nuclei were stained with Tropro-3 (blue fluorescence), according to an exemplary embodiment of the invention.
Figure 3A:
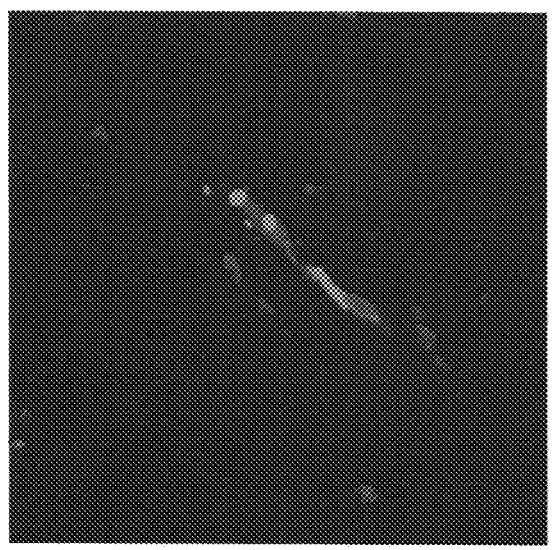

Clear evidence was found for homing of the injected human EPCs to sites of shock wave treatment (right hind limb, FIG. 3a). EPCs were found incorporated into vessels structures (FIG. 3a, upper left panel, dotted line). A higher magnification is given in FIG. 3a, lower left panel.

Figure 3B:
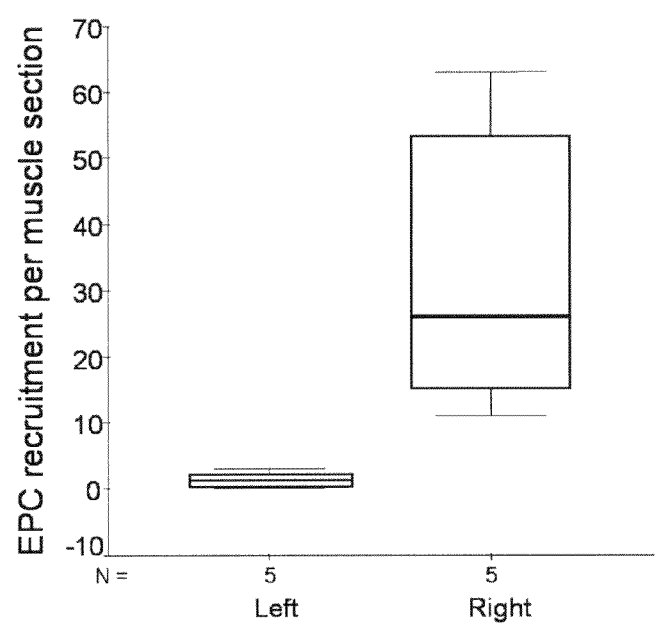
FIG. 3B is a block diagram depicting quantification of intravenously injected EPCs that were recruited to shock wave treated muscles, according to an exemplary embodiment of the invention.

Quantification of the incorporated EPC indicated that a markedly and significantly higher number of EPCs were incorporated in the shock wave-treated vasculature as compared to the untreated tissue (FIG. 3b). Thus, these data provide proof-of-concept for shock wave-induced attraction of infused ex-vivo cultured stem and progenitor cells.

In patients with chronic tissue damage such as previous myocardial infarction, the recruitment of stem/progenitor cells is markedly reduced due to the low expression of chemoattractant factors in the target tissue. Therefore, to provide evidence for the functional relevance of the shock wave-facilitated recruitment of EPCs, a rat model of chronic hind limb ischemia was used.

Hind limb ischemia model. The in vivo neovascularization capacity of infused human EPC was investigated in a rat model of hind limb ischemia, by use of 5 wk old athymic nude rats (Charles River Laboratory) weighing 100-120 g. The proximal portion of the femoral artery including the superficial and the deep branch as well as the distal portion of the saphenous artery were occluded using an electrical coagulator. The overlying skin was closed using surgical staples. Three weeks after induction of hind limb ischemia, chronic ischemia was assessed by Laser Doppler imaging. Only rats with evidence for chronic ischemia were randomized for one of the four treatment groups:

| Group | Shock wave pretreatment | EPC infusion |
| --- | --- | --- |
| 1 | − | − |
| 2 | − | + |
| 3 | + | − |
| 4 | + | + |

EPCs were infused 24 hours after shock wave pretreatment.

Limb perfusion measurements. After two weeks, the ischemic (right)/non-ischemic (left) limb blood flow ratio was determined using a laser Doppler blood flow imager (Laser Doppler Perfusion Imager System, moorLDI™-Mark 2, Moor Instruments, Wilmington, Del.). Before initiating scanning, mice were placed on a heating pad at 37° C. to minimize variations in temperature. After twice recording laser Doppler color images, the average perfusions of the ischemic and non-ischemic limb were calculated. To minimize variables including ambient light and temperature, calculated perfusion is expressed as the ratio of ischemic to non-ischemic hind limb perfusion.

Figure 4A:
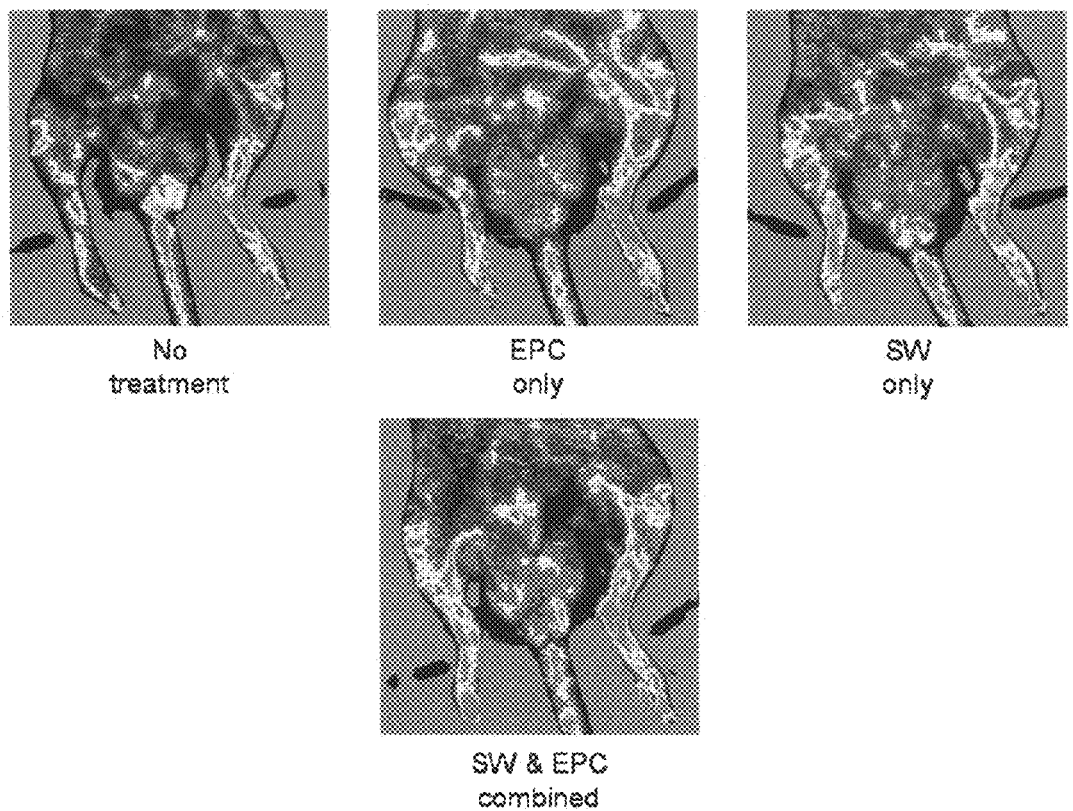
FIG. 4A is a series of representative images of the ischemic (left) and non-ischemic (right) limb for animals that received either no treatment, EPC infusion only, shock wave pretreatment only, or both, according to an exemplary embodiment of the invention.
Figure 4B:
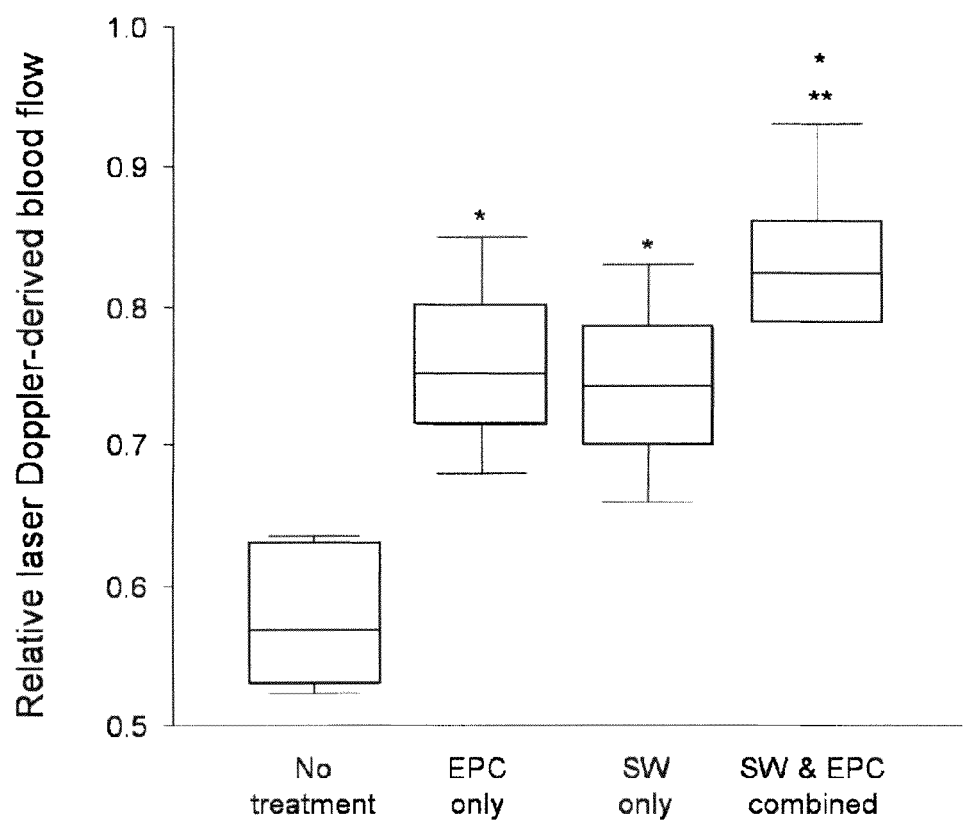
FIG. 4B is a block diagram depicting quantitative perfusion data generated by calculating the ratio of the perfusion of the ischemic to the non-ischemic limb, according to an exemplary embodiment of the invention.

The data indicate that either EPC injection alone or shock wave pretreatment alone significantly enhance limb perfusion as compared to untreated control animals (FIGS. 4A and 4B). However, limb perfusion was further enhanced by the combined treatment of the animals. These data provide evidence for the functional impact of shock wave-facilitated recruitment of EPC.

What is claimed is:

1. A method for treating a patient having an ischemic tissue disease comprising
    administering an endothelial progenitor cell (EPC) directly to the ischemic tissue, wherein the EPC is of the same species;
    subjecting the patient to extracorporeal shock wave treatment thereby inducing expression of at least one chemoattractant factor in a tissue of the patient affected by the disease; and
    observing neovascularization in the treated patient.

2. The method of claim 1, wherein the EPC is suitable for being administered to the patient before, during or after the application of extracorporeal shock wave to the patient.

3. The method of claim 1, wherein the ischemic tissue disease is a cardiovascular disease.

4. The method of claim 3, wherein the cardiovascular disease is a dilatative cardiomyopathy.

5. The method of claim 4, wherein the cardiovascular disease is a myocardial infarction or an ischemic cardiomyopathy.

6. The method of claim 1, wherein the ischemic tissue disease is a neurological disease.

7. The method of claim 6, wherein the neurological disease is a peripheral neuropathy or neuropathic pain.

8. The method of claim 1, wherein the ischemic tissue disease is a skeletal muscle disease.

9. The method of claim 1, wherein the cell therapy is targeted to an ischemic tissue located in the heart or in a skeletal muscle.

10. The method of claim 1, wherein said at least one chemoattractant factor is vascular endothelial growth factor (VEGF), or stromal cell derived factor 1 (SDF-1).

11. The method of claim 1, wherein the EPC is derived from embryonic stem cells or umbilical cord blood stem and/or progenitor cells.

12. The method of claim 1, wherein the EPC is derived from adult stem cells and/or adult progenitor cells.

13. The method of claim 12, wherein the adult stem and/or progenitor cells are derived from a source selected from the group consisting of bone marrow, peripheral blood, and organs.

14. The method of claim 1, wherein the EPC is applied by way of systemic infusion, local arterial infusion, venous infusion or by direct injection into the affected tissue.

* * * * *